United States Patent [19]

Vincent et al.

[11] Patent Number: 5,286,732
[45] Date of Patent: Feb. 15, 1994

[54] NITROGEN-CONTAINING BICYCLIC COMPOUNDS AND PHARMACEUTICAL COMPOSITIONS THEREOF

[75] Inventors: Michel Vincent, Bagneux; Georges Remond, Versailles; Bernard Portevin, Elancourt; Yolande Herve, Puteaux; Jean Lepagnol, Chatou; Guillaume de Nanteuil, Suresnes, all of France

[73] Assignee: Adir et Compagnie, Courbevoie, France

[21] Appl. No.: 950,958

[22] Filed: Sep. 25, 1992

[30] Foreign Application Priority Data

Sep. 27, 1991 [FR] France .................... 91 11893

[51] Int. Cl.$^5$ .............. A61K 31/40; A61K 31/47; C07D 401/06
[52] U.S. Cl. ........................ 514/299; 514/307; 514/314; 514/414; 546/112; 546/164; 546/165; 546/169; 546/146; 548/468
[58] Field of Search ........... 514/299, 307, 314, 414; 546/112, 164, 165, 169, 146; 548/468

[56] References Cited

FOREIGN PATENT DOCUMENTS 0288685 11/1988 European Pat. Off. .
320753 6/1989 European Pat. Off. .
0321956 6/1989 European Pat. Off. .
0345428 12/1989 European Pat. Off. .
394989 10/1990 European Pat. Off. .
9118891 12/1991 PCT Int'l Appl. .

OTHER PUBLICATIONS

*Chemical Abstracts* vol. 115 No. 19 abstract 201789f (1991).
*Chemical Abstracts* vol 116 No. 17 abstract 166086w (1992).
J. Enzyme Inhibition 5, 51–75 (1991), Saito, M. et al., "Synthesis and Inhibitory Activity of Acylpeptidyl-pyrrolidine Derivatives . . . ".
Weingartner, et al., "Effects of Vasopressin on Human Memory Functions", Science, vol. 211, pp. 601–603 (1981).
Mazurek, et al., "CSF Vasopressin Concentration Is Reduced in Alzheimer's Disease", Neurology, vol. 36, pp. 1133–1137 (1986).
Aoyagi, et al., "Deficiency of Kallikrein–Like Enzyme Activities in Cerebral Tissue of Patients with Alzheimer's Disease", Experientia, vol. 46, pp. 94–97 (1990)
Yoshimoto, et al., "Proline Specific Endopeptidase from Flavobacterium", Agric. Biol. Chem. vol. 42(12), pp. 2417–2419 (1978).

*Primary Examiner*—Mary C. Lee
*Assistant Examiner*—Jacqueline Haley
*Attorney, Agent, or Firm*—Gordon W. Hueschen

[57] ABSTRACT

The invention relates to the compounds of formula (I):

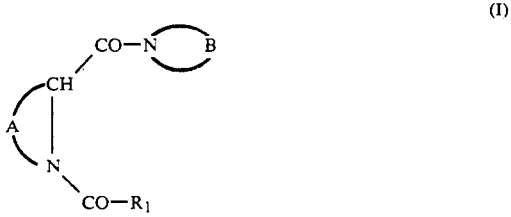

in which:
  A represents, with the nitrogen and carbon atoms to which it is bound, a heterocycle,
  B represents, with the nitrogen atom to which it is bound, a heterocycle,
  $R_1$ represents alkoxy, benzyloxy, phenoxy, substituted or unsubstituted alkyl, substituted or unsubstituted alkenyl or substituted or unsubstituted cycloalkyl, their enantiomers, diastereoisomers and epimers as well as their addition salts with a pharmaceutically acceptable acid, medicinal products containing the same.

12 Claims, No Drawings

NITROGEN-CONTAINING BICYCLIC COMPOUNDS AND PHARMACEUTICAL COMPOSITIONS THEREOF

The present invention relates to new nitrogen-containing bicyclic compounds.

Ageing of the population by increasing life expectancy is making the problem of age-related cerebral ageing and senile dementias increasingly important. Consequently, the search for new therapeutic compounds capable of preventing memory deficiencies and neuropsycho-behavioral disorders of ageing has become a priority.

Besides the conventional neurotransmitters (acetylcholine and norepinephrine) which are involved in memory functions, there are neuropeptides such as vasopressin (AVP) or thyrotropin releasing hormone (TRH) which also exert memory-enhancing effects by acting as neuromodulators in addition to their peripheral or endocrinal role (Science, 211, 601, 1981).

Studies have recently shown that the cerebral levels of these peptides decrease significantly in patients suffering from senile dementia (Neurobiology, 36, 1133, 1986).

Even more recently, it was observed that the activity of prolylendopeptidase, a key enzyme in the catabolism of these peptides, substantially increases (+100 %) in the brain of Alzheimer patients (Experientia, 46, 94, 1990). Consequently, it has been suggested and demonstrated that prolylendopeptidase-inhibitors can prevent memory deficiencies by enhancing the promnesic effect of certain neuropeptides and in particular vasopressin. These results were observed especially during experimental amnesia using scopolamine. For the inhibitory compounds studied, an excellent correlation has been reported (EP 321 956) between the prolylendopeptidase-inhibiting effect and the learning-enhancing effect.

It was therefore particularly important to synthesize new compounds possessing a prolylendopeptidase-inhibiting activity (or post-prolyl cleaving enzyme: PPCE).

The compounds of the present invention, in addition to being new, have proved particularly advantageous by virtue of the intensity and duration of their properties of inhibiting prolyendopeptidase and thereby preventing the degradation of natural neuropeptides involved in memory functions. Their activity is higher both in vitro and in vivo than that of compounds described in the prior art, such as for example the compounds described in Patents EP 321 956 and EP 345 428 as PPCE inhibitors. It is also substantially higher than that of reference nootropic agents also known for inhibiting PPCE activity, such as for example the compounds described in Patent EP 288 685.

The compounds of the invention are therefore useful in the prevention and treatment, on the one hand, of behavioral, especially memory, disorders associated with ageing and acute or chronic degenerative neuronal diseases and, on the other hand, of psychic disorders associated with anxiety and depression.

The invention relates more particularly to new nitrogen-containing bicyclic compounds of general formula (I):

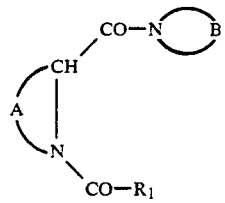

(I)

in which:

A represents, with the carbon and nitrogen atoms to which it is attached, any one of the following heterocycles:

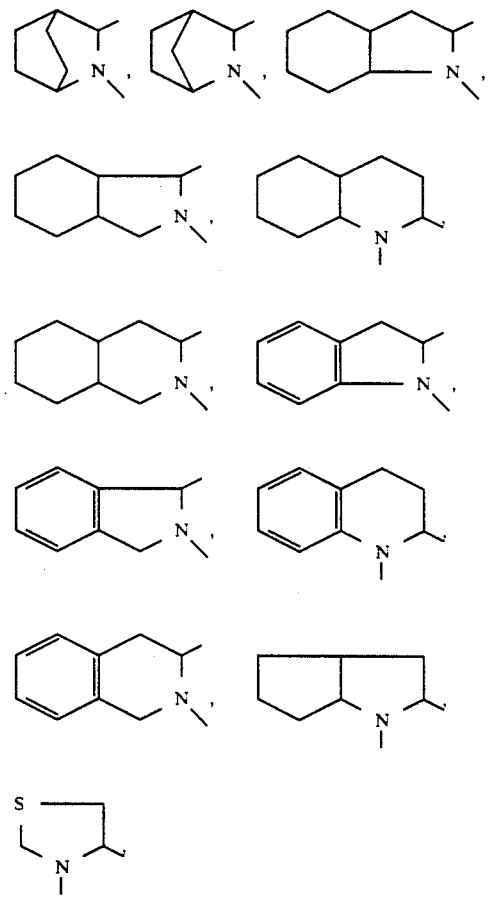

B represents, with the nitrogen atom to which it is attached, any one of the following heterocycles:

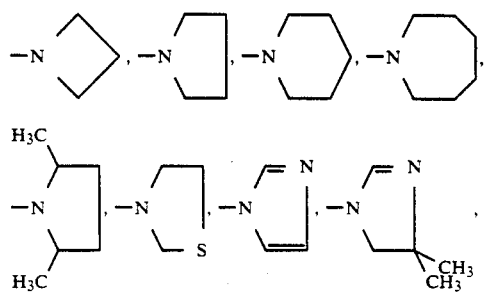

-continued

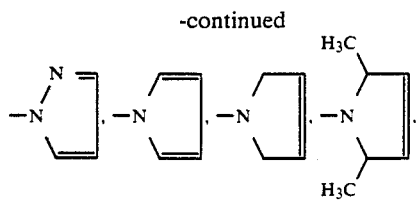

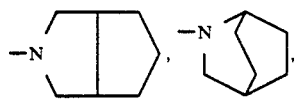

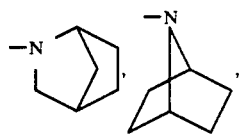

$R_1$ represents a linear or branched ($C_1$-$C_6$)alkyl group, a benzyloxy group, a phenoxy group or a linear or branched ($C_1$-$C_6$) alkyl group, a linear or branched ($C_2$-$C_6$) alkenyl group or a $C_3$-$C_7$ cycloalkyl group, each of the alkyl, alkenyl or cycloalkyl groups being optionally substituted by one or more groups, which are identical or different: phenyl, naphthyl, $C_3$-$C_7$ cycloalkyl, ($C_3$-$C_7$) phenylcycloalkyl, trifluoromethyl, ($C_3$-$C_7$-dicycloalkyl)methylthio,

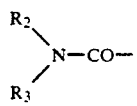

(in which $R_2$ and $R_3$, which are identical or different, represent a hydrogen atom, a phenyl, benzyl or ($C_3$-$C_7$ dicycloalkyl)methyl group),

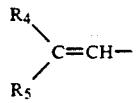

(in which
$R_4$ represents a phenyl, ($C_3$-$C_7$)cycloalkyl or ($C_3$-$C_7$ dicycloalkyl)methyl group,
$R_5$ represents a hydrogen atom, a phenyl, ($C_3$-$C_7$) cycloalkyl or trifluoromethyl group),
provided that:
when A represents, with the carbon and nitrogen atoms to which it is attached, a 1,3-thiazolidine ring,
$R_1$ represents a linear or branched ($C_1$-$C_6$)alkyl group which is substituted by at least any one of the following groups:
($C_3$-$C_7$) cycloalkyl,
($C_3$-$C_7$) phenylcycloalkyl,
trifluoromethyl,
(trifluoromethylphenyl)methyl,
($C_3$-$C_7$ dicycloalkyl)methylthio,

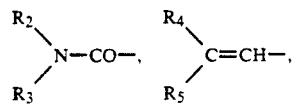

or alternatively $R_1$ represents a ($C_3$-$C_7$) phenylcycloalkyl

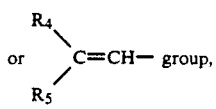

when B represents, with the nitrogen atom to which it is attached, a pyrrolidine ring,
$R_1$ represents any one of the following groups:
tert-butoxy,
phenylcyclopropyl,
a linear or branched ($C_1$-$C_6$)alkyl or a linear or branched ($C_2$-$C_6$) alkenyl, each of the alkyl or alkenyl groups still being substituted by at least one ($C_3$-$C_7$ dicycloalkyl)methyl, ($C_3$-$C_7$ dicycloalkyl) methylthio,

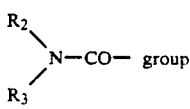

or by two ($C_3$-$C_7$) cycloalkyl groups,
a linear Or branched ($C_1$-$C_6$) trifluoromethylalkyl,
a linear or branched ($C_1$-$C_6$) trifluoromethylalkenyl which are optionally substituted by one or more phenyl or ($C_3$-$C_7$) cycloalkyl groups,
when A represents, with the carbon and nitrogen atoms to which it is attached, a 2,3-dihydroindole ring and B represents, with the nitrogen atom to which it is attached, a pyrrolidine ring, then $R_1$ is different from a 3-phenylpropyl group,
their enantiomers, diastereoisomers and epimers as well as their addition salts with a pharmaceutically acceptable acid.

Among the pharmaceutically acceptable acids, there may be mentioned, with no limitation being implied, hydrochloric, sulfuric, tartaric, maleic, fumaric, methanesulfonic and camphoric acids and the like.

The invention also encompasses the process for preparing the compounds of formula (I), wherein an acid of formula (II), whose isomers have optionally been separated using a conventional separation technique:

in which A has the same meaning as in formula (I) and $R'_1$ represents a linear or branched ($C_1$-$C_6$) alkoxy group or a benzyloxy group, is reacted with an amine of formula (III), whose isomers have optionally been separated using a conventional separation technique, according to a peptide-coupling technique like that described by W. KONIG and R. GEIGER (Ber, 103, 788, 1970):

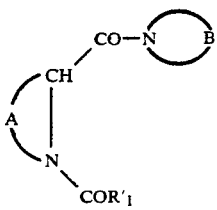

(III)

in which B has the same meaning as in formula (I), to give the compound of formula (I/a), which is a specific example of the compounds of formula (I):

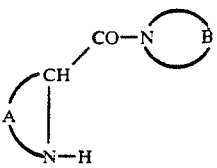

(I/a)

in which A, B and $R'_1$ have the same meaning as above, which compound is deprotected, if desired, by a conventional deprotection technique, to give the amine of formula (IV):

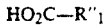

(IV)

in which A and B have the same meaning as in formula (I), which amine is reacted with an acid of formula (V), in the presence of a conventional coupling agent for peptide synthesis:

$$HO_2C-R''_1 \quad (V)$$

in which:

$R''_1$ has the same meaning as $R_1$, except in the case where $R_1$ represents $R'_1$, to give the compound of formula (I/b), which is a specific example of the compounds of formula (I):

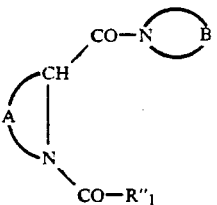

(I/b)

in which A, B and $R''_1$ have the same meaning as above, which compounds of formula (I/a) and (I/b) are purified, where appropriate, by a conventional purification technique, whose isomers are separated, if desired, by a conventional separation technique and which are converted, if required, to their addition salts with a pharmaceutically acceptable acid.

The compounds of the invention possess very advantageous pharmacological properties. They strongly inhibit prolylendopeptidase activity, thus making them useful in the treatment of memory and cognitive disorders and neurobehavioral disorders associated with ageing and acute or chronic degenerative diseases of the nervous system such as Alzheimer's, Pick's or Korsakoff's disease, vasculocerebral accidents, spinal trauma or amyotrophic lateral sclerosis. They are similarly useful in the treatment of psychic disorders associated with anxiety and depression.

The subject of the present invention is also the pharmaceutical compositions containing, as active ingredient, at least one compound of general formula (I) or one of its addition salts with a pharmacologically acceptable acid, alone or in combination with one or more inert, nontoxic excipients or vehicles.

Of the pharmaceutical compositions according to the invention, there may be mentioned more particularly those which are suitable for oral, parenteral or nasal administration, ordinary or sugared tablets, sublingual tablets, sachets, packets, gelatin capsules, glossettes, lozenges, suppositories, creams, ointments, skin gels and the like.

The dosage varies according to the age and weight of the patient, the nature and severity of the condition as well as the administration route.

The latter may be oral, nasal, rectal or parenteral. Generally, the unit dosage ranges between 0.5 and 100 mg for a treatment using 1 to 3 doses per 24 hours.

The following examples illustrate the invention and do not imply any limitation thereto.

Preparations A to N do not lead to the compounds of the invention but to starting products which are useful in the preparation of the compounds of formula (I).

PREPARATION A 3,3-Dicyclopropylpropanoic acid

STAGE A: 3,3-Dicyclopropylpropionitrile 209 g of 2,2-dicyclopropylethanol tosylate (prepared from 2,2-dicyclopropylethanol and para-toluenesulfonyl chloride) in solution in 45 ml of DMSO, are slowly added to 40 g of sodium cyanide in 45 ml of dimethyl sulfoxide (DMSO), with stirring and at 95° C. The heating is continued for one hour. After filtration of the precipitate and washing with ethyl ether, the filtrates are pooled, washed with a saturated solution of sodium chloride, dried and evaporated. The expected product is obtained after distillation under vacuum.

Yield: 90%

Boiling point: 95°-100° C. (15 mm/Hg)

Refractive index: $n_D^{22.5} = 1.457$

STAGE B: 3,3-Dicyclopropylpropanoic acid 45 g of potassium hydroxide are dissolved in 65 ml of water. 100 ml of diethylene glycol are added to the above solution followed by 30 g of the product obtained in stage A. The mixture is refluxed until the evolution of ammonia ceases. After cooling, 700 ml of water are added and the mixture is acidified with 12 N hydrochloric acid. After extraction with ether, the ethereal phases are pooled, washed with water until neutral, dried and evaporated. The expected product is obtained after distillation.

Yield: 83%

Boiling point: 138°-142° C. (13 mm/Hg)

Refractive index: $n_D^{27} = 1.458$

PREPARATION B 4,4-Dicyclopropylbutanoic acid

STAGE A: 1-Bromo-3,3-dicyclopropylpropane 15.5 g of phosphorus tribromide are slowly added to a solution, cooled to −30° C., of 22 g of 3,3-dicyclopropylpropanol (obtained by reduction of the compound described in preparation A in the presence of lithium aluminum hydride) in 85 ml of anhydrous ether, and the mixture is poured, after returning to room temperature, into 7 ml of ice cold water. The organic phase is then washed with a saturated solution of sodium bicarbonate and then with water until neutral and finally dried and evaporated. The expected product is obtained after distillation under vacuum.

Yield: 60%
Boiling point: 101°–105° C. (18 mm/Hg)

STAGE B: 4,4-Dicyclopropylbutyronitrile

The expected product is obtained by reacting potassium cyanide with the compound described in the preceding stage, in an ethanol/water mixture.

Yield: 73%
Boiling point: 114°–117° C. (17 mm/Hg)

STAGE C: 4,4-Dicyclopropylbutanoic acid

The expected product is obtained by carrying out the procedure as in stage B of preparation A using the compound described in the preceding stage.

Yield: 74%
Boiling point: 170°–172° C. (16 mm/Hg)

PREPARATION C:

5,5-Dicyclopropylpentanoic acid

The expected product is obtained using the procedure described in Org. Synthesis Coll. Vol. II, 474, from the 1-bromo-3,3-dicyclopropylpropane described in stage A of preparation B.

Yield: 74%
Boiling point: 170°–172° C. (16 mm/Hg)

PREPARATION D 6,6-Dicyclopropylhexanoic acid

The expected product is obtained using the process described in preparation B.

PREPARATION E 5,5-Dicyclopropylpropen-4-oic acid 20 mmol of (carboxypropyl)triphenylphosphonium iodide are placed in 100 ml of anhydrous tetrahydrofuran. 40 ml of a 1 M solution of potassium tert-butoxide in THF are added dropwise to the above mixture, under a nitrogen atmosphere.

Stirring is continued for 30 minutes and a solution containing 20 mmol of dicyclopropyl ketone in 20 ml of anhydrous THF is added. The mixture is left stirring for 4 days at room temperature. After taking up in water, filtration of the triphenylphosphine oxide and washing with dichloromethane, the aqueous phase is acidified with 6 N HCl and extracted with dichloromethane. The organic phases are washed with water, dried and evaporated. The expected product is obtained after purification by chromatography on silica gel, using as eluent a dichloromethane/ethanol mixture (97/3).

Yield: 50%
Infrared (liquid film) $v_{co}=1743$ and $1711$ cm$^{-1}$

PREPARATION F 6,6-Dicyclopropylhexen-5-oic acid

The expected product is obtained by carrying out the procedure as in preparation E, from (carboxybutyl) triphenylphosphonium bromide.

Yield: 55%
Infrared (liquid film) $v_{co}=1709$ cm$^{-1}$

PREPARATION G 6,6-Dicyclopropylhexen-4-oic acid

The expected product is obtained by carrying out the procedure as in preparation E, from 2,2-dicyclopropylacetaldehyde.

Yield: 54%
Infrared (nujol) $v_{co}=1712$ cm$^{-1}$

PREPARATION H

3-Trifluoromethylcinnamic acid

STAGE A: Ethyl 3-trifluoromethylcinnamate 450 mmol of sodium hydride are placed in 50 ml of anhydrous diglyme. A solution of 84 g of triethylphosphonoacetate in 300 ml of diglyme is added to this mixture at room temperature. Stirring is continued until the evolution of hydrogen has ceased and then a solution containing 52 g of trifluoroacetophenone in 100 ml of diglyme is added. After refluxing for 18 hours, the mixture is cooled to 10° C. and poured into 500 ml of water. After extraction with ethyl ether, drying and evaporation, the expected product is purified by distillation.

Yield: 67%
Boiling point: 104°–108° C. (18 mm/Hg)

STAGE B: 3-Trifluoromethylcinnamic acid

The expected product is obtained by saponification of the compound described in the preceding stage.

Yield: 92%
Melting point: 95° C.

PREPARATION I

3-Phenyl 3-trifluoromethylpropanoic acid

The expected product is obtained by catalytic hydrogenation, in ethanolic medium, of the compound described in stage A of preparation A, using palladized carbon as catalyst, followed by saponification.

Yield: 90%
Melting point: 72° C.

PREPARATION J

4-Phenyl 4-trifluoromethylbutanoic acid

The expected product is obtained by carrying out the procedure as in preparation B, from 3-phenyl-3-trifluoromethylpropanol (itself obtained by reduction of ethyl 3-phenyl-3-trifluoromethylpropanoate).

Infrared (nujol) $v_{co}=1728$ cm$^{1}$

PREPARATION K:

5-Phenyl-5 trifluoromethylpentanoic acid

The expected product is obtained by carrying out the procedure as in preparation B, from 4-phenyl-4-trifluoromethylbutanol (itself obtained by reduction of the compound obtained in preparation J).

Boiling point: 106°–110° C. (16 mm/Hg)

PREPARATION L

5-Cyclopentyl-5-trifluoromethylpentanoic acid

The expected product is obtained by carrying out the procedure as in preparation B, from 4-cyclopentyl-4-trifluoromethylbutanol.

PREPARATION M 3-(Dicyclopropylmethylthio)propanoic acid

STAGE A: Methyl 3-(dicyclopropylmethylthio)propionate

A solution containing 6.8 g of dicyclopropylmercaptan (obtained by reduction, with sodium borohydride, of dicyclopropylthioketone, itself prepared by the action of LAWESSON reagent on dicyclopropyl ketone) in 10 ml of ethanol is added to a solution of sodium ethoxide. After stirring for 10 minutes, 10 g of methyl 3-bromopropionate in 10 ml of ethanol are added to the above mixture. The mixture is kept stirring for 18 hours at room temperature. The expected product is obtained after filtration of the sodium bromide, evaporation and distillation.

Yield: 66%

Boiling point: 158°–160° C. (16 mm/Hg)

STAGE B: 3-(Dicyclopropylmethylthio)propanoic acid

The expected product is obtained by saponification of the compound described in the preceding stage.

Yield: 84%

Infrared (liquid film) $v_{co}=1711$ cm$^{-1}$

PREPARATION N

3-Dicyclopropylmethylamino carbonylpropanoic acid

The expected product is obtained by peptide coupling of dicyclopropylmethylamine with methyl monosuccinate according to the technique described by W. KONIG and R. GEIGER (Ber, 103, 788, 1970), followed by saponification.

Infrared (nujol):

$v_{co}$ (acid) = 1703 cm$^{-1}$ $v_{co}$ (acid) = 1631 cm$^{-1}$

EXAMPLE 1

(3S)-2-Aza 2-tert-butyloxycarbonyl-3-[(pyrrolidin-1-yl)carbonyl]-bicyclo[2.2.2]octane Using the peptide coupling technique (dicyclo-hexyl-carbodiimide/hydroxybenzotriazole-DCC/HOBT) described by W. KONIG and R. GEIGER (Ber. 103, 788, 1970) and dimethylformamide as solvent, the expected product which is purified by crystallization from ethyl acetate, is prepared from pyrrolidine and (3S)-2-aza-2-tert- butyloxycarbonylbicyclo [2.2.2]octane-3-carboxylic acid.

Yield: 73%

Melting point: 150°–152° C.

Specific rotation: $[\alpha]D^{20} = -10.5°$ (c=1%, EtOH)

| | Elemental microanalysis: | | |
|---|---|---|---|
| | C % | H % | N % |
| Calculated | 66.20 | 9.15 | 9.08 |
| Found | 66.24 | 9.40 | 9.06 |

EXAMPLE 2

(3R)-2-Aza 2-tert-butyloxycarbonyl 3-[(pyrrolidin-1-yl)carbonyl]bicyclo[2.2.2]octane The expected product is obtained according to the same process as that described in Example 1 but using the (3R) isomer of 2-aza-2-tert-butyloxycarbonylbicyclo[2.2.2]octane-3-carboxylic acid in place of the (3S) isomer.

Melting point: 150°–152° C.

| | Elemental microanalysis: | | |
|---|---|---|---|
| | C % | H % | N % |
| Calculated | 66.20 | 9.15 | 9.08 |
| Found | 66.93 | 9.15 | 9.18 |

Examples 3 to 6 were obtained according to the process described in Example 1, using the corresponding known starting products.

EXAMPLE 3

(1S,3S,4R)-2-Aza-2-tert butyloxycarbonyl-3-[(pyrrolidin-1-yl)carbonyl]bicyclo[2.2.1]heptane Melting point: 142°–144° C.

EXAMPLE 4

(3S)-2-Aza-2-tert-butyloxycarbonyl 3-[(3-azabicyclo[3.3.0]octane-3 yl)carbonyl]bicyclo[2.2.2]octane Melting point: 154°–156° C.

| | Elemental microanalysis: | | |
|---|---|---|---|
| | C % | H % | N % |
| Calculated | 68.93 | 9.26 | 8.04 |
| Found | 68.99 | 9.25 | 8.04 |

EXAMPLE 5

(2S,3aS,7aS) 1-(4 Phenylbutyryl) 2-[(pyrrolidin 1-yl)carbonyl]perhydroindole

| | Elemental microanalysis: | | |
|---|---|---|---|
| | C % | H % | N % |
| Calculated | 67.05 | 9.38 | 8.69 |
| Found | 66.60 | 9.52 | 8.70 |

EXAMPLE 6

(1R, 3S, 4R)-2-Aza-2-tert butyloxycarbonyl-3-[(pyrrolidin-1-yl)carbonyl]bicyclo[2.2.1]heptane Melting point: 112° C.

| | Elemental microanalysis: | | |
|---|---|---|---|
| | C % | H % | N % |
| Calculated | 65.28 | 8.90 | 9.52 |
| Found | 65.28 | 8.82 | 9.68 |

EXAMPLE 7

(3S)-2-Aza-2-(4-phenylbutyryl)-3-[(pyrrolidin-1-yl)carbonyl]bicyclo[2.2.2]octane STAGE A: (3S)-2-Aza-3-[(pyrrolidin-1-yl)carbonyl]-bicyclo[2.2.2]octane 37 mmol of the compound described in Example 1 are dissolved in 100 ml of anhydrous ethyl acetate. A stream of hydrochloric acid is passed through while keeping the temperature at 20° C., and stirring is continued for 18 hours at room temperature. The solvent is evaporated and the residue is taken up in 100 ml of water. The insoluble matter is filtered and, after alkalization by adding sodium bicarbonate, the filtrate is concentrated to dryness. The residue is finally taken up in 100 ml of ethanol, 100 ml of dichloromethane and then 100 ml of ethyl ether, successively. The expected product is obtained after filtration of the salts and evaporation.

Yield: 89%
Melting point: 117° C.

STAGE B: (3S)-2-Aza-2-(4-phenylbutyryl)-3-[(pyrrolidin-1-yl)carbonyl]bicyclo[2.2.2]octane The expected product is obtained according to the same process as that described in Example 1, but using 4-phenylbutyric acid and the product obtained in stage A. It is purified by chromatography on silica, using as elution solvent a dichloromethane/methanol mixture (95/5), and crystallized from an acetone-isopropyl ether mixture.

Melting point: 77° C.

| | Elemental microanalysis: | | |
|---|---|---|---|
| | C % | H % | N % |
| Calculated | 74.54 | 8.53 | 7.90 |
| Found | 74.71 | 8.56 | 7.93 |

Examples 8 to 34 were obtained according to the process described in Example 7, using the known corresponding starting products or those described in preparations A to N.

EXAMPLE 8

(3R)-2-Aza-2-(4-phenylbutyryl)-3-[(pyrrolidin-1-yl)carbonyl]bicyclo[2.2.2]octane Melting point: 70° C.

EXAMPLE 9

(1S,3S,4R) 2 Aza-2-(4-phenylbutyryl)-3-[(pyrrolidin-1-yl)carbonyl]bicyclo[2.2.1]heptane Infrared (nujol):$\nu_{co}$ (amide)=1650 cm$^{-1}$

EXAMPLE 10

(2S, 3aS, 7aS)-1-tert-Butyloxycarbonyl-2-[(pyrrolidin-1-yl)carbonyl]perhydroindole

| | Elemental microanalysis: | | |
|---|---|---|---|
| | C % | H % | N % |
| Calculated | 74.96 | 8.75 | 7.60 |
| Found | 74.57 | 9.16 | 7.16 |

EXAMPLE 11

(3S)-2-(4-Phenylbutyryl)-3-[(pyrrolidin-1-yl)carbonyl]1,2,3,4-tetrahydroisoquinoline

| | Elemental microanalysis: | | |
|---|---|---|---|
| | C % | H % | N % |
| Calculated | 76.56 | 7.50 | 7.44 |
| Found | 76.07 | 6.99 | 7.20 |

EXAMPLE 12

(3S)-2-Aza-2-[5,5-(dicyclopropyl)pentanoyl]-3-[(pyrrolidin-1-yl)carbonyl]bicyclo[2.2.2]octane

| | Elemental microanalysis: | | |
|---|---|---|---|
| | C % | H % | N % |
| Calculated | 74.15 | 9.74 | 7.52 |
| Found | 74.22 | 10.15 | 7.62 |

EXAMPLE 13

(3S)-2-Aza-2-[6,6-(dicyclopropyl)hexanoyl]-3-[(pyrrolidin-1-yl)carbonyl]bicyclo[2.2.2]octane Melting point: 86° C.

EXAMPLE 14

(2S, 3aS, 7aS)-1-[5,5-dicyclopropyl)pentanoyl]-2-[(pyrrolidin-1-yl)carbonyl]perhydroindole

| | Elemental microanalysis: | | |
|---|---|---|---|
| | C % | H % | N % |
| Calculated | 74.57 | 9.91 | 7.25 |
| Found | 74.04 | 9.99 | 7.29 |

EXAMPLE 15

(2S, 3aS, 7aS)-1-[3,3-dicyclopropyl)propionyl]-2-[(pyrrolidin-1-yl)carbonyl]perhydroindole Melting point: 110°-112° C.

| | Elemental microanalysis: | | |
|---|---|---|---|
| | C % | H % | N % |
| Calculated | 73.70 | 9.56 | 7.81 |
| Found | 73.36 | 9.61 | 8.14 |

EXAMPLE 16

(2S, 3aS, 7aS)-1-[4,4-Dicyclopropyl)butyryl]-2-[(pyrrolidin-1-yl)carbonyl]perhydroindole

| | Elemental microanalysis: | | |
|---|---|---|---|
| | C % | H % | N % |
| Calculated | 74.15 | 9.74 | 7.52 |
| Found | 73.81 | 9.64 | 7.68 |

EXAMPLE 17

(1S, 3S, 4R)-2-[5,5-dicyclopropyl)pentanoyl]-3-[(pyrrolidin-1-yl)carbonyl]bicyclo[2.2.1]heptane

| | Elemental microanalysis: | | |
|---|---|---|---|
| | C % | H % | N % |
| Calculated | 73.70 | 9.56 | 7.81 |
| Found | 73.93 | 9.55 | 7.82 |

EXAMPLE 18

(3S)-2-Aza-2-[6,6-(dicyclopropyl)hexen-5-oyl]-3-[(pyrrolidin-1-yl)carbonyl]bicyclo[2.2.2]octane Infrared (nujol):
$v_{co}$ (amide)=1676 and 1653 cm$^{-1}$ $v_{co}$=1630 cm$^{-1}$

EXAMPLE 19

(3S)-2-Aza 2 [(E)-cinnamoyl]3-[(pyrrolidin-1-yl)carbonyl]bicyclo[2.2.2]octane

Melting point: 184° C.

EXAMPLE 20

(3S) 2 Aza-2 [(E) 4-phenylbuten-3-oyl]-3-[(pyrrolidin-1-yl)carbonyl]bicyclo[2.2.2]octane Melting point: 100°–105° C.

EXAMPLE 21

(3S)-2-Aza-2-[5,5-(dicyclopropyl)penten-4-oyl]-3-[(pyrrolidin-1-yl)carbonyl]bicyclo[2.2.2]octane Infrared (nujol): $v_{co}$ (amide)=1656 and 1637 cm$^{-1}$

EXAMPLE 22

(2S,3aS,7aS)-1-(3-Trifluoromethylcinnamoyl)-2-[-[(pyrrolidin-1-yl)carbonyl]perhydroindole Melting point: 148° C.

| | Elemental microanalysis: | | |
|---|---|---|---|
| | C % | H % | N % |
| Calculated | 65.70 | 6.47 | 6.66 |
| Found | 65.66 | 6.64 | 6.75 |

EXAMPLE 23

(2S, 3aS, 7aS)-1-(3-Trifluoromethyl-3-phenyl-propanoyl)-2-[(pyrrolidin-1-yl)carbonyl]perhydroindole, α isomer Melting point: 134° C.

| | Elemental microanalysis: | | |
|---|---|---|---|
| | C % | H % | N % |
| Calculated | 65.38 | 6.91 | 6.63 |
| Found | 65.46 | 6.93 | 6.66 |

EXAMPLE 24

(2S, 3aS, 7aS)-1-(3-Trifluoromethyl-3-phenyl-propanoyl)-2-[(pyrrolidin-1-yl)carbonyl]perhydroindole, β isomer Melting point: 98° C.

| | Elemental microanalysis: | | |
|---|---|---|---|
| | C % | H % | N % |
| Calculated | 65.38 | 6.91 | 6.63 |
| Found | 65.42 | 6.99 | 6.51 |

EXAMPLE 25

(2S, 3aS, 7aS)-1-(3-Trifluoromethyl-4-phenylbutanoyl]-2-[(pyrrolidin-1-yl)carbonyl]perhydroindole

| | Elemental microanalysis: | | |
|---|---|---|---|
| | C % | H % | N % |
| Calculated | 66.04 | 7.16 | 6.42 |
| Found | 65.78 | 7.18 | 6.25 |

EXAMPLE 26

(2S, 3aS, 7aS)-1-[(R,S)-5-Trifluoromethyl-5-phenylpentanoyl]-2-[(pyrrolidin-1-yl)carbonyl-yl]perhydroindole

| | Elemental microanalysis: | | |
|---|---|---|---|
| | C % | H % | N % |
| Calculated | 66.65 | 7.38 | 6.22 |
| Found | 66.97 | 7.60 | 6.14 |

EXAMPLE 27

(3S)-2-Aza-2-benzyloxycarbonyl-3-[(pyrrolidin-1-yl)carbonyl]bicyclo[2.2.2]octane Melting point: 105° C.

| | Elemental microanalysis: | | |
|---|---|---|---|
| | C % | H % | N % |
| Calculated | 70.15 | 7.65 | 8.18 |
| Found | 70.04 | 7.50 | 8.17 |

EXAMPLE 28

(2S, 3aS, 7aS)-1-(3-Dicyclopropylmethylthio)propanoyl]-2-[(pyrrolidin-1-yl)carbonyl]perhydroindole

| | Elemental microanalysis: | | | |
|---|---|---|---|---|
| | C % | H % | N % | S % |
| Calculated | 68.28 | 8.97 | 6.92 | 7.92 |
| Found | 67.85 | 9.18 | 7.11 | 7.76 |

EXAMPLE 29

(3S)-2-Aza-2-[3-(N-Benzylanilinocarbonyl)propionyl]-3-[(pyrrolidin-1-yl) carbonyl]bicyclo[2.2.2]octane

| | Elemental microanalysis: | | |
|---|---|---|---|
| | C % | H % | N % |
| Calculated | 73.54 | 7.45 | 8.87 |
| Found | 72.35 | 7.37 | 8.92 |

EXAMPLE 30

(3S, 2-Aza-2-[3-Dicyclopropylmethylaminocarbonyl)propionyl]-3-[(pyrrolidin-1-yl)carbonyl]bicyclo[2.2.2]octane

| | Elemental microanalysis: | | |
|---|---|---|---|
| | C % | H % | N % |
| Calculated | 68.80 | 8.79 | 10.46 |
| Found | 68.96 | 8.81 | 10.47 |

EXAMPLE 31

(3S, 2-Aza-2-[((1S, 2S)-2-phenylcycloprop-1-yl)carbonyl]-3-[(pyrrolidin-1-yl)carbonyl]bicyclo[2.2.2]octane Specific rotation: $[\alpha]D^{1.5}_2 = +163.7°$ (c=1%, ethanol)

| | Elemental microanalysis: | | |
|---|---|---|---|
| | C % | H % | N % |
| Calculated | 74.97 | 8.01 | 7.95 |
| Found | 75.05 | 8.10 | 7.71 |

EXAMPLE 32

(3S)-2-Aza-2-[((1R,2R)2-phenylcycloprop-1-yl)carbonyl]-3-[(pyrrolidin-1-yl)carbonyl]bicyclo[2.2.2]octane Specific rotation: $[\alpha]D^{1.5}_2 = -148.1°$ (c=1%, ethanol)

| | Elemental microanalysis: | | |
|---|---|---|---|
| | C % | H % | N % |
| Calculated | 74.97 | 8.01 | 7.95 |
| Found | 74.73 | 8.10 | 7.67 |

EXAMPLE 33

(3S)-2-Aza-2 (6,6-dicyclopropylhexen 4-oyl)-3-[(pyrrolidin 1-yl)carbonyl]bicyclo[2.2.2]octane Infrared (liquid film) $\nu_{co}$ (amide) = 1639 cm$^{-1}$

EXAMPLE 34

(2S,3aS,7aS)-1-(5-cyclopentyl-5-trifluoromethylpentanoyl) -2-[(pyrrolidin 1 yl)carbonyl]perhydroindole

| | Elemental microanalysis: | | |
|---|---|---|---|
| | C % | H % | N % |
| Calculated | 65.13 | 8.43 | 6.33 |
| Found | 65.05 | 8.43 | 6.34 |

Examples 35 to 43 were obtained according to the process described in Example 1, but using the corresponding starting products.

EXAMPLE 35

(2S,3aS,7aS)-1-tert Butyloxycarbonyl 2-[(azetidin-1-yl)carbonyl]perhydroindole

Melting point: 130° C.

| | Elemental microanalysis: | | |
|---|---|---|---|
| | C % | H % | N % |
| Calculated | 66.20 | 9.15 | 9.08 |
| Found | 66.13 | 9.21 | 8.94 |

EXAMPLE 36

(2S,3a S,7a S)-1-tert-Butyloxycarbonyl-2-[(piperidin-1-yl)carbonyl]perhydroindole Melting point: 132° C.

| | Elemental microanalysis: | | |
|---|---|---|---|
| | C % | H % | N % |
| Calculated | 67.82 | 9.59 | 8.33 |
| Found | 67.53 | 9.58 | 8.40 |

EXAMPLE 37

(2S,3a S,7aS)-1-tert-Butyloxycarbonyl-2-[homopiperidin-1-yl)carbonyl]perhydroindole Melting point: 122° C.

| | Elemental microanalysis: | | |
|---|---|---|---|
| | C % | H % | N % |
| Calculated | 68.54 | 9.78 | 7.99 |
| Found | 68.20 | 9.64 | 7.79 |

EXAMPLE 38

(2S,3a S,7aS)-1-tert-Butyloxycarbonyl-2-[(2-azabicyclo[2.2.2]octan-2-yl)carbonyl]perhydroindole Melting point: 150°-152° C.

| | Elemental microanalysis: | | |
|---|---|---|---|
| | C % | H % | N % |
| Calculated | 69.58 | 9.45 | 7.73 |
| Found | 69.58 | 9.56 | 8.07 |

EXAMPLE 39

(3S)-2-Aza-2-tert-butyloxycarbonyl-3-[thiazolidin-3-yl)carbonyl]bicyclo[2.2.2]octane Melting point: 174° C.

| | Elemental microanalysis: | | | |
|---|---|---|---|---|
| | C % | H % | N % | S % |
| Calculated | 58.87 | 8.03 | 8.58 | 9.82 |
| Found | 59.11 | 8.27 | 8.73 | 9.14 |

EXAMPLE 40

(3S)-2-Aza-2-tert-Butyloxycarbonyl-3-[(pyrrolin-1-yl)carbonyl]bicyclo[2.2.2]octane Melting point: 190° C.

| | Elemental microanalysis: | | |
|---|---|---|---|
| | C % | H % | N % |
| Calculated | 66.64 | 8.55 | 9.14 |
| Found | 66.76 | 8.52 | 9.24 |

EXAMPLE 41

(3S) 2-Aza-2 [5,5-(dicyclopropyl)pentanoyl]-3-[(thiazolidin-3 yl)carbonyl]bicyclo[2.2.2]octane Melting point: 98°–100° C.
Infrared (nujol) $v_{co}$ (amide) = 1635 cm$^{-1}$

EXAMPLE 42

(3S) 2-Aza-2 (4-phenylbutyryl)-3-[(imidazol1-yl)carbonyl]bicyclo[2.2.2]octane

| | Elemental microanalysis: | | |
|---|---|---|---|
| | C % | H % | N % |
| Calculated | 71.77 | 7.17 | 11.96 |
| Found | 71.95 | 7.22 | 12.03 |

EXAMPLE 43

(3S)-2-Aza-2-(4 phenylbutyryl)-2 [pyrazol-2-yl)carbonyl]bicyclo[2.2.2]octane

Infrared (nujol) $v_{co}$ (amide) = 1637 cm$^{-1}$

EXAMPLE 44

(2S,3aS,7aS) 1 (5 phenyl-5-trifluoromethylpentanoyl) -2-[(pyrrolidin-1- yl)carbonyl]perhydroindole, α isomer

EXAMPLE 45

(2S,3aS,7aS)-1-(5-phenyl 5 trifluoromethylpentanoyl) -2-[(pyrrolidin-1- yl)carbonyl]perhydroindole, β isomer Examples 44 and 45 were prepared by separation of the isomers of Example 26 by chromatography on silica gel, using as eluent a 70/30 toluene-ethyl acetate mixture. The isomers were termed α and β according to the order in which they leave the column.

The isomeric purity of both compounds was monitored on a chiral column (Chiralpak; length=25 cm, inner diameter=4.6 mm, particle size=10 μm), using as elution solvent a heptane/isopropanol/diethylamine mixture (85/15/0.05).
Example 44: retention time=12.3 min.
Example 45: retention time=10.8 min.

EXAMPLE 46

3-[5,5-Dicyclopropylpentanoyl]-4-[2,5-dihydropyrrol -1-yl)carbonyl]thiazolidine

Example 46 was prepared according to the process described in Example 7.

Examples 47 to 58 were synthesized according to the process described in Example 7, using the corresponding starting products.

EXAMPLE 47

(1S,3S,4R) 2-Aza-2-[((1S,2S)-2-phenylcycloprop-1-yl)carbonyl]-3-[(pyrrolidin-1-yl)carbonyl]bicyclo[2.2.1]heptane Melting point: 175° C.

| | Elemental microanalysis: | | |
|---|---|---|---|
| | C % | H % | N % |
| Calculated | 74.53 | 7.74 | 8.28 |
| Found | 74.45 | 7.68 | 8.16 |

EXAMPLE 48

(1S,3S,4R)-2-Aza-2-[((1R,2R)-2-phenylcycloprop-1-yl)carbonyl]-3-[(pyrrolidin-1-yl)carbonyl]bicyclo[2.2.1]heptane Melting point: 153° C.

| | Elemental microanalysis: | | |
|---|---|---|---|
| | C % | H % | N % |
| Calculated | 74.53 | 7.74 | 8.28 |
| Found | 74.44 | 7.92 | 7.95 |

EXAMPLE 49

2S,3aS,7aS) 1 [((1S,2S) 2-phenylcycloprop-1-yl)carbonyl]-2-[(pyrrolidin-1-yl)carbonyl]perhydroindole Melting point: 142° C.

| | Elemental microanalysis: | | |
|---|---|---|---|
| | C % | H % | N % |
| Calculated | 75.38 | 8.25 | 7.64 |
| Found | 75.37 | 8.27 | 7.65 |

EXAMPLE 50

(2S,3aS,7aS) 1 [((1R,2R) 2 phenylcycloprop-1-yl)carbonyl]-2-[(pyrrolidin-1-yl)carbonyl]perhydroindole Melting point: 170° C.

| | Elemental microanalysis: | | |
|---|---|---|---|
| | C % | H % | N % |
| Calculated | 75.38 | 8.25 | 7.64 |
| Found | 75.04 | 8.32 | 7.58 |

EXAMPLE 51

(4R) 3-[((1S,2S)-2-phenylcycloprop-1-yl)carbonyl]-4-[(pyrrolidin-1-yl)carbonyl]thiazolidine Melting point: 134° C.

EXAMPLE 52

(4R)-3-[((1R,2R)-2-phenylcycloprop-1 yl)carbonyl]4-[(pyrrolidin-1-yl)carbonyl]thiazolidine Melting point: 200° C.

The compounds of Examples 31, 47, 49, 51, 53, 55, 57 and 32, 48, 50, 52, 54, 56, 58 may also be obtained from 2-phenylcycloprop -1-yl-carboxylic acids of the respective (1S,2S) and (1R,2R) configuration, prepared according to the process described in "Optical resolution for Chemical compounds" (Volume 2, part I/Optical Resolution Information Center, Manhattan College, Riverdale—N.Y. 10471, USA).

EXAMPLE 53

(2S,3aS,7aS)-1-[((1S,2S)-2-phenylcycloprop-1-yl)carbonyl]-2-[(2,5-dihydropyrrolin-1-yl)carbonyl]perhydroindole

EXAMPLE 54

(2S,3aS,7aS)-1-[((1R,2R)-2 phenylcycloprop-1-yl)carbonyl]-2-[(2,5-dihydropyrrolin-1-yl)carbonyl]perhydroindole Infrared (nujol) $\nu_{co}$ (amide) et $\nu_{c=c}$=between 1660 and 1624 cm$^{-1}$

EXAMPLE 55

(2S,3aS,7aS)-1 [((1S,2S) 2-phenylcycloprop-1-yl)carbonyl]-2-[(1,3-thiazolidin-3-yl)carbonyl]perhydroindole

EXAMPLE 56

(2S,3aS,7aS)-1-[((1R,2R)-2-phenylcycloprop-1 -yl)carbonyl]-2-[(1,3-thiazolidin-3-yl)carbonyl]perhydroindole

| | Elemental microanalysis : | | | |
|---|---|---|---|---|
| | C % | H % | N % | S % |
| calculated | 68.72 | 7.34 | 7.28 | 8.34 |
| found | 68.64 | 7.47 | 7.98 | 8.10 |

EXAMPLE 57

(2S,3aS,7aS)-[(1S,2S)-2-phenylcycloprop 1-yl)carbonyl]-2-[(pyrrol-1 yl)carbonyl]perhydroindole

EXAMPLE 58

(2S,3aS,7aS)-[(1R,2R)-2 phenylcycloprop-1-yl)carbonyl]-2 [(pyrrol 1 yl)carbonyl]perhydroindole

| | Elemental microanalysis : | | |
|---|---|---|---|
| | C % | H % | N % |
| calculated | 76.21 | 7.23 | 7.73 |
| found | 75.68 | 7.11 | 7.41 |

PHARMACOLOGICAL STUDY OF THE COMPOUNDS OF THE INVENTION

EXAMPLE 59

Measurement of the anti-prolylendopeptidase activity

The method of Yoshimoto and Tsuru (Agr. Biol. Chem., 42, 2417, 1978) was used. Prolylendopeptidase is isolated from Flavobacterium meningosepticum. The enzymatic substrate is Z-Gly-Pro-pNitroaniline.

A mixture of 0.1 M phosphate buffer (pH 7; 0.99 ml), 2 M (0.25 ml) substrate and a solution of the inhibitory compound to be tested (0.01 ml) is incubated at 37° C. for 5 minutes. 0.1 ml of a solution of prolylendopeptidase (0.5 U/ml) is then added and the mixture is allowed to stand at 37° C. for 10 minutes. The enzymatic reaction is stopped by addition of 2 ml of a 1 M solution of Triton X-100-acetate buffer (pH 4). After allowing to stand at room temperature, the absorbance is measured at 410 nm.

A control measurement is performed by replacing the solution of test compound with the same volume of phosphate buffer. The percentage inhibition of the enzyme is calculated from this control measurement. For each compound tested, the concentration which inhibits prolylendopeptidase by 50% (IC$_{50}$) is determined.

The compounds of the invention were compared to the two reference compounds, known for their high prolylendopeptidase-inhibiting activity and initially described for this purpose: ONO1603 (EP 345 428) and N-(4-phenylbutanoyl)-L-thiaprolylpyrrolidineimide (Example 3: EP 321 956), called hereinbelow ZERIA.

The compounds of the invention exert a very high prolylendopeptidase-inhibiting activity, greater than the reference compounds as indicated in the table of IC$_{50}$ values:

| ZERIA | 5,4 × 10$^{-7}$ M | | |
|---|---|---|---|
| ONO1603 | 5.7 × 10$^{-7}$ M | Example 32 | 5 × 10$^{-8}$ M |
| Example 7 | 5 × 10$^{-8}$ M | Example 45 | 3.8 × 10$^{-9}$ M |
| Example 9 | 2.7 × 10$^{-8}$ M | Example 48 | 1.4 × 10$^{-8}$ M |
| Example 10 | 3.4 × 10$^{-8}$ M | Example 50 | 1.2 × 10$^{-8}$ M |
| Example 12 | 9 × 10$^{-9}$ M | Example 54 | 2 × 10$^{-8}$ M |
| Example 17 | 2.6 × 10$^{-8}$ M | Example 56 | 1.3 × 10$^{-8}$ M |

EXAMPLE 60

The measurement of prolylendopeptidase inhibition was performed in vitro and in vivo in rat cerebral cortex by means of a substrate similar to a peptide naturally cleaved by prolylendopeptidase, thyrotropin-releasing hormone (TRH).

An extract of cerebral cortex is prepared by grinding the tissue in phosphate buffer (25 mM NaH$_2$PO$_4$; 2 mM DTT; 0.5 mM EDTA-2K) in an amount of 5 ml/g.

After centrifugation, 200 μl of supernatant are incubated for 15 minutes, at 37° C., in a final volume of 2.1 ml, to which 250 μl of substrate (TRH-p-nitroaniline) are added for another incubation of 20 minutes, followed immediately by an absorbance reading at 410 nm.

The product tested is either added to the cortex extract before the first incubation (determination of the IC$_{50}$ in vitro) or administered by the IP route 30 minutes before the preparation of the tissue extract.

Under the test conditions, the compounds of the invention strongly inhibit the prolylendopeptidase of rat cerebral cortex both in vitro and after administration in vivo. Here again, this activity is substantially higher than that for the reference compounds.

| | IC$_{50}$ in vitro | Inhibition in vivo | |
|---|---|---|---|
| | | dose (mg/kg) | % |
| ZERIA | 5.4 × 10$^{-8}$ M | 30 | 47 |
| | | 10 | 16 |
| ONO 1603 | 5.7 × 10$^{-8}$ M | 30 | 19 |
| | | 10 | 5 |
| Example 5 | 5 × 10$^{-7}$ M | 30 | 65 |
| Example 10 | 3.4 × 10$^{-8}$ M | 30 | 58 |
| Example 12 | 9 × 10$^{-10}$ M | 30 | 38 |
| Example 32 | 5 × 10$^{-9}$ M | 10 | 62 |
| | | 2.5 | 37 |
| Example 50 | 1 × 10$^{-9}$ M | 0.3 | 60 |
| Example 52 | 2.10$^{-8}$ M | 5 | 35 |
| Example 54 | 2.4 × 10$^{-9}$ M | 0.6 | 57 |
| Example 56 | 1.3 × 10$^{-9}$ M | 0.6 | 58 |

EXAMPLE 61

The duration of action of the compounds with respect to the inhibition in vivo of prolylendopeptidase in rat cerebral cortex was estimated according to the same method as in Example 58, by IP administration of the tested compounds at various times before preparing the tissue extract. The time for which the inhibitory effect is equal to 50% of the maximum effect (measured at 30 minutes) was calculated (t ½).

Similarly, the oral bioavailability of the compounds of the invention was estimated by IP or oral administration, 30 minutes or 60 minutes before measuring the inhibitory effect. The oral bioavailability index (IBO) was determined by dividing the inhibitory effect (%) measured after oral administration by that measured after IP administration. The most active compounds of the invention exert their effects according to a duration of cerebral action which is much longer than that for the reference compounds and with a much higher oral bioavailability, which endows them with considerable therapeutic usefulness.

|  | dose (mg/kg) | t ½ | IBO |
| --- | --- | --- | --- |
| ZERIA | 30 | 1 hour | 0.30 |
| ONO 1603 | 30 | 1 hour | <0.30 |
| Example 5 | 15 | 2 hours | 0.40 |
| Example 10 | 30 | 2 hours | 0.40 |
| Example 32 | 2.5 | 7 hours | 0.75 |
| Example 50 | 0.15 | 7 hours | 0.85 |
| Example 54 | 0.6 | 7 hours | 0.80 |
| Example 56 | 0.6 | 7 hours | 0.80 |

PHARMACEUTICAL COMPOSITION
EXAMPLE 62

Tablet: Preparation formula for 1000 tablets in 10-mg doses

| Compound of Example 1 | 10 g |
| --- | --- |
| Hydroxypropyl cellulose | 2 g |
| Wheat starch | 10 g |
| Lactose | 100 g |
| Magnesium stearate | 3 g |
| Talc | 3 g |

We claim:
1. A compound selected from those of formula (I):

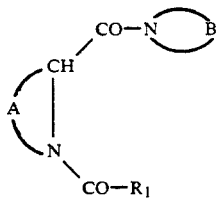

in which:
A represents, with the carbon and nitrogen atoms to which it is attached, a heterocycle selected from the group consisting of.
B represents, with the nitrogen atom to which it is attached, a heterocycle selected from the group consisting of:

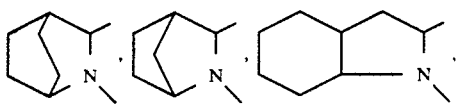

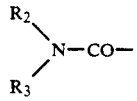
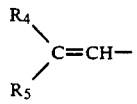

-continued

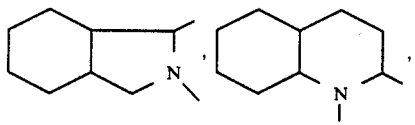

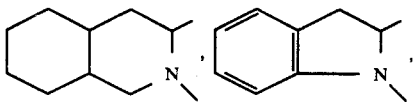

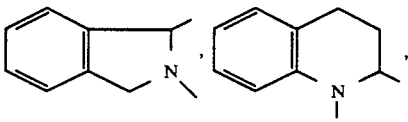

B represents, with the nitrogen atom to which it is attached, a heterocycle selected from the group consisting of:

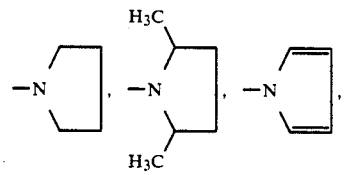

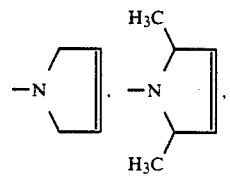

$R_1$ represents linear or branched ($C_1$-$C_6$) alkoxy, benzyloxy, phenoxy, or linear or branched ($C_1$-$C_6$) alkyl, or branched ($C_2$-$C_6$) alkenyl, or ($C_3$-$C_7$) cycloalkyl, each of the alkyl, alkenyl, or cycloalkyl being optionally substituted by one or more groups, which are identical or different selected from:

phenyl, napthyl, ($C_3$-$C_7$) cycloalkyl, ($C_3$-$C_7$) phenylcycloalkyl, trifluoromethyl, (di$C_3$-$C_7$ cycloalkyl)methylthio, $$\begin{matrix} R_2 \\ \phantom{R_2}\diagdown \\ \phantom{R_2}\phantom{\diagdown}N-CO- \\ \phantom{R_2}\diagup \\ R_3 \end{matrix}$$

in which $R_2$ and $R_3$, which are different, represent hydrogen, phenyl, benzyl, or ($C_3$-$C_7$) cycloalkyl)methyl, $$\begin{matrix} R_4 \\ \phantom{R_4}\diagdown \\ \phantom{R_4}\phantom{\diagdown}C=CH- \\ \phantom{R_4}\diagup \\ R_5 \end{matrix}$$

in which
$R_4$ represents phenyl, ($C_3$-$C_7$)cycloalkyl, or (di$C_3$-$C_7$ cycloalkyl)methyl, and $R_5$ represents hydrogen, phenyl, ($C_3$–$C_7$) cycloalkyl, or trifluoromethyl, provided that:

when B represents, with the nitrogen atom to which it is attached, a pyrrolidine ring, $R_1$ represents any one of the following groups
tert-butoxy,
phenylcyclopropyl,
linear or branched ($C_1$–$C_6$)alkyl or linear or branched ($C_2$–$C_6$) alkenyl,
each of the alkyl or alkenyl still being substituted by at least one ($C_3$–$C_7$ dicycloalkyl)methyl, (di $C_3$–$C_7$ dicycloalkyl) methylthio,

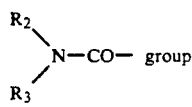

or by two ($C_3$–$C_7$) cycloalkyl,
linear or branched ($C_1$–$C_6$) trifluoromethylalkyl,
linear or branched ($C_1$–$C_6$) trifluoromethylalkenyl which are optionally substituted by one or more phenyl or ($C_3$–$C_7$) cycloalkyl, when A represents, with the carbon and nitrogen atoms to which it is attached, a 2,3-dihydroindole ring and B represents, with the nitrogen atom to which it is attached, a pyrrolidine ring, $R_1$ is different from 3-phenylalkyl, their enantiomers, diastereoisomers and epimers, as well as their addition salts with a pharmaceutically-acceptable acid.

2. A compound of claim 1, wherein A represents, with the carbon and nitrogen atoms to which it is attached, a 2-azabicyclo[2.2.2]octane ring, its enantiomers, diastereoisomers and epimers, as well as its addition salts with a pharmaceutically-acceptable acid.

3. A compound of claim 1, wherein A represents, with the carbon and nitrogen atoms to which it is attached, a 2-azabicyclo[2.2.1]heptane ring, its enantiomers, diastereoisomers and epimers, as well as its addition salts with a pharmaceutically-acceptable acid.

4. A compound of claim 1, wherein A represents, with the carbon and nitrogen atoms to which it is attached, a perhydroindole ring, its enantiomers, diastereoisomers and epimers, as well as its addition salts with a pharmaceutically-acceptable acid.

5. A compound of claim 1, wherein B represents, with the nitrogen atom to which it is attached, a pyrrolidine ring, its enantiomers, diastereoisomers and epimers, as well as its addition salts with a pharmaceutically-acceptable acid.

6. A compound of claim 1, wherein B represents, with the nitrogen atom to which it is attached, a 2,5-dihydropyrrole ring, its enantiomers, diastereoisomers and epimers, as well as its addition salts with a pharmaceutically-acceptable acid.

7. A compound of claim 1, wherein $R_1$ represents phenylcyclopropyl, its enantiomers, diastereoisomers and epimers, as well as its addition salts with a pharmaceutically-acceptable acid.

8. The compound of claim 1, which is 2-aza-[(2-phenylcycloprop-1-yl)carbonyl]-3-[(pyrrolidin-1-yl) carbonyl]bicyclo[2.2.2]octane, its enantiomers, diastereoisomers and epimers, as well as its addition salts with a pharmaceutically-acceptable acid.

9. The compound of claim 1, which is 2-aza-2-[(2-phenylcycloprop-1-yl)carbonyl]-3-[(pyrrolidin-1-yl) carbonyl]bicyclo[2.2.1]heptane, its enantiomers, diastereoisomers and epimers, as well as its addition salts with a pharmaceutically-acceptable acid.

10. The compound of claim 1, which is 1-[(2-phenylcycloprop-1-yl)carbonyl]-2-[(pyrrolidin-yl) carbonyl]-perhydroindole, its enantiomers, diastereoisomers and epimers, as well as its addition salts with a pharmaceutically-acceptable acid.

11. A method for treating a mammal afflicted with a condition requiring a prolylendopeptidase inhibitor comprising the step of administering to the mammal an amount of a compound of claim 1 which is effective for alleviation of said condition.

12. A pharmaceutical composition useful as a prolylendopeptidase inhibitor comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,286,732            Page 1 of 5
DATED      : Feb. 15, 1994
INVENTOR(S) : Michel Vincent, et al It is certified that error appears in the above-indentified patent and that said Letters Patent is hereby corrected as shown below:

Title page, [57]; insert -- OF THE DISCLOSURE -- after "ABSTRACT" and, in the last line, insert the word -- and -- before "medicinal".
Col. 3, line 21; "$(C_1-C_6)$alkyl" should read -- $(C_1-C_6)$alkoxy --.
Col. 3, line 24; insert a parenthesis, -- ( --, before "$C_3-C_7$)".
Col. 3, line 28; indent this line and insert a parenthesis, -- ( --, before "$C_3-C_7$)".
Col. 3, line 29; delete the hyphen between "$(C_3-C_7$" and "dicy-".
Col. 4, line 28; "Or" should read -- or --.
Col. 4, line 31; "$(C_{3-c7})$" should read -- $(C_3-C_7)$ --.
Col. 5, Formula (III); "H-N    B" should read
-- H-N͡ B --.
Col. 6, line 64; center "PREPARATION B" in the column.
Col. 7, line 34; insert an empty line before and center "PREPARATION D" in the column.
Col. 8, line 33; insert a hyphen between "3-Phenyl" and "3".
Col. 8, line 43; insert a hyphen between "4-Phenyl" and "4".
Col. 8, line 51; insert a hyphen after "5-Phenyl-5".
Col. 9, line 24; delete the space between "Dicyclopropylmethyl-amino" and "carbonylpropanoic".
Col. 9, line 36; insert a hyphen at the end of this line, after "Aza".
Col. 9, line 40; delete the hyphen between "(dicyclo" and "hexyl-".
Col. 9, line 61; insert a hyphen between "Aza" and "2" and another at the end of the line, after "butyloxycarbonyl".
Col. 10, line 13; insert a hyphen between "tert" and "butyloxy-carbonyl".
Col. 10, line 19; insert a hyphen between "butyloxycarbonyl" and "3".
Col. 10, line 20; insert a hyphen at the end of this line.

UNITED STATES PATENT AND TRADEMARK OFFICE
CERTIFICATE OF CORRECTION

PATENT NO. : 5,286,732
DATED : Feb. 15, 1994
INVENTOR(S) : Michel Vincent, et al It is certified that error appears in the above-indentified patent and that said Letters Patent is hereby corrected as shown below:

Col. 10, line 32; insert a hyphen between "(2S,3aS,7aS)" and "1", between "(4" and "Phenylbutyryl)", between "Phenyl-butyryl)" and "2-", and at the end of the line.

Col. 10, line 43; insert a hyphen before "butyloxycarbonyl".

Col. 11, line 40; "(1S,3S,4R) 2" should read -- (1S,3S,4R)-2- --

Col. 12, line 48; insert a parenthesis, -- ( --, before "Dicyclopropyl).

Col. 12, line 60; "2-[5,5-dicyclopropyl)" should read -- 2-Aza-2-[5,5-(dicyclopropyl) --.

Col. 13, line 4; insert a hyphen between "rolidin" and "1-yl)".

Col. 13, line 7; "$v_{co}=1630$ cm$^{-1}$" should read -- $v_{co}=1630$ cm$^{-1}$ -- and should appear on the following line.

Col. 13, line 10; insert a hyphen after "Aza" and at the end of the line.

Col. 13, line 11; insert a hyphen between "[(E)-cinnamoyl]" and "3".

Col. 13, line 17; "(3S) 2 Aza-2 [(E)" should read -- (3S)-2-Aza-2-[(E)- --.

Col. 13, line 30; delete the hyphen and bracket between "-2" and "-[(pyr-".

Col. 14, line 5; "7aS)-1-(3-Trifluoromethyl" should read --7aS)-1-[(R,S)-4-Trifluoromethyl --.

Col. 14, line 20; delete the "-yl" after "carbonyl".

Col. 14, line 45; "-(3-Dicyclopropylmethylthio)" should read -- -[3-(Dicyclopropylmethylthio) --.

Col. 15, line 3; "(3S, 2-" should read -- (3S)-2- --.

Col. 15, line 16; "(3S, 2-" should read -- (3S)-2- --.

Col. 15, line 31; insert a hyphen at the end of this line, after "[((1R,2R)".

Col. 15, line 45; insert a hyphen after "(3S)-2-Aza-2" and at the end of the line.

Col. 15, line 46; insert a hyphen after "pyrrolidin".

UNITED STATES PATENT AND TRADEMARK OFFICE
CERTIFICATE OF CORRECTION

PATENT NO. : 5,286,732  
DATED : Feb. 15, 1994  
INVENTOR(S) : Michel Vincent, et al It is certified that error appears in the above-indentified patent and that said Letters Patent is hereby corrected as shown below:

Col. 15, line 52; "(pyrrolidin 1 yl)" should read -- (pyrrolidin-1-yl) --.  
Col. 15, line 66; insert a hyphen both before and after "Butyl-oxycarbonyl".  
Col. 16, line 10; insert -- S)- -- at the end of this line.  
Col. 16, line 11; delete "S)-" from the beginning of this line.  
Col. 16, line 24; insert -- S, -- at the end of this line.  
Col. 16, line 25; delete "S," from the beginning of this line.  
Col. 16, line 38; insert -- S, -- at the end of this line.  
Col. 16, line 39; delete "S," from the beginning of this line.  
Col. 17, line 10; insert a hyphen after "(3S)" and at the end of the line.  
Col. 17, line 11; insert a hyphen at the end of the line, after "[(thiazolidin-3".  
Col. 17, line 18; insert a hyphen after "(3S)" and at the end of the line.  
Col. 17, line 19; "(imidazoll-yl)" should read -- (imidazol-1-yl) --.  
Col. 17, line 30; insert a hyphen before "phenylbutyryl" and at the end of the line.  
Col. 17, line 35; "1 (5 phenyl" should read -- -1-(5-phenyl --.  
Col. 17, line 37; insert the word -- and -- at the beginning of this line, before the centered "EXAMPLE 45".  
Col. 17, line 39; "(5-phenyl 5" should read -- (5-phenyl-5- --.  
Col. 17, line 65; insert a hyphen after "(1S,3S,4R)".  
Col. 18, line 24; "1 [((1S,2S)" should read -- -1-[((1S,2S)- --  
Col. 18, line 37; "1 [((1R,2R) 2" should read -- -1-[((1R,2R)-2- --.  
Col. 18, line 51; insert a hyphen after "(4R)".  
Col. 18, line 57; insert a hyphen at the end of this line, after "phenylcycloprop-1".  
Col. 18, line 58; insert a hyphen after "yl)carbonyl]".

UNITED STATES PATENT AND TRADEMARK OFFICE
CERTIFICATE OF CORRECTION

PATENT NO. : 5,286,732    Page 4 of 5
DATED : Feb. 15, 1994
INVENTOR(S) : Michel Vincent, et al It is certified that error appears in the above-indentified patent and that said Letters Patent is hereby corrected as shown below:

Col. 19, line 7; insert a hyphen at the end of this line, after "(1R,2R)-2".
Col. 19, line 15; insert a hyphen both before and after "[((1S,2S)".
Col. 19, line 32; insert a hyphen at the end of this line, after "phenylcycloprop".
Col. 19, line 33; insert a hyphen after "(pyrrol-1".
Col. 19, line 35; insert a hyphen at the end of the line, after "[(1R,2R)-2".
Col. 19, line 36; "2 [(pyrrol 1" should read -- 2-[(pyrrol-1- --
Col. 20, line 6; "ON01603" should read -- ONO1603 --.
Col. 21, line 58; replace the period at the end of this line with a colon.
Col. 21, lines 59-61 ; starting with "B represents" delete these lines.
Col. 22, line 20; after the last formula, insert the following two formulas:  and 
Col. 22, line 42; after "alkyl, " insert -- linear --.
Col. 22, line 58; delete the parenthesis, ")" at the end of this line, after "($C_3$-$C_7$".
Col. 23, line 12; "($C_{3-c7}$" should read -- ($C_3$-$C_7$ --.
Col. 23, line 13; "$C_{3-c7}$ dicycloalkyl" should read -- $C_3$-$C_7$ cycloalkyl--.
Col. 23, line 20; "($C_{3-c7}$)" should read -- ($C_3$-$C_7$) --.
Col. 23, line 24; "($C_{3-c7}$)" should read -- ($C_3$-$C_7$) --.
Col. 23, line 25; insert the word -- or -- before "when A".

UNITED STATES PATENT AND TRADEMARK OFFICE
CERTIFICATE OF CORRECTION

PATENT NO. : 5,286,732
DATED : Feb. 15, 1994
INVENTOR(S) : Michel Vincent, et al It is certified that error appears in the above-indentified patent and that said Letters Patent is hereby corrected as shown below:

Col. 24, line 30; "(pyrrolidin-yl) carbonyl]-" should read -- (pyrrolidin-1-yl) carbonyl] --.

Signed and Sealed this

Sixth Day of September, 1994

Attest:

BRUCE LEHMAN

Attesting Officer

Commissioner of Patents and Trademarks